(12) United States Patent
Pedersen

(10) Patent No.: US 10,034,792 B2
(45) Date of Patent: Jul. 31, 2018

(54) LOCKING RING WITH LEVER ARM

(71) Applicant: Coloplast A/S, Humlebaek (DK)

(72) Inventor: Troels Pedersen, Nivaa (DK)

(73) Assignee: Coloplast A/S, Humlebaek (DK)

( * ) Notice: Subject to any disclaimer, the term of this patent is extended or adjusted under 35 U.S.C. 154(b) by 409 days.

(21) Appl. No.: 14/383,112

(22) PCT Filed: Mar. 6, 2013

(86) PCT No.: PCT/DK2013/050058
§ 371 (c)(1),
(2) Date: Sep. 5, 2014

(87) PCT Pub. No.: WO2013/131523
PCT Pub. Date: Sep. 12, 2013

(65) Prior Publication Data
US 2015/0045755 A1    Feb. 12, 2015

(30) Foreign Application Priority Data

Mar. 6, 2012 (DK) ................................ 2012 70101

(51) Int. Cl.
*A61F 5/448* (2006.01)

(52) U.S. Cl.
CPC ...... *A61F 5/448* (2013.01); *A61F 2005/4483* (2013.01); *A61F 2005/4486* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,796,063 A | * | 6/1957 | Smelser | A61F 5/448 604/342 |
| 3,964,485 A | * | 6/1976 | Neumeier | A61F 5/448 604/342 |
| 4,664,661 A | * | 5/1987 | Ferguson | A61F 5/448 604/342 |
| 4,826,496 A | * | 5/1989 | Ferguson | A61F 5/448 604/339 |
| 4,917,691 A | * | 4/1990 | Briggs | A61F 5/448 604/339 |
| 4,929,245 A | * | 5/1990 | Holtermann | A61F 5/448 604/338 |
| 5,026,360 A | * | 6/1991 | Johnsen | A61F 5/448 292/256.69 |
| 5,322,522 A | * | 6/1994 | Olsen | A61F 5/448 604/332 |
| 5,322,523 A | | 6/1994 | Olsen | |

(Continued)

FOREIGN PATENT DOCUMENTS

| WO | 9418919 | 9/1994 |
|---|---|---|
| WO | 0209629 | 2/2002 |

*Primary Examiner* — Todd J Scherbel
*Assistant Examiner* — Guy K Townsend
(74) *Attorney, Agent, or Firm* — Coloplast Corp., Coloplast A/S; Nick Baumann

(57) ABSTRACT

A locking ring (1) for an ostomy coupling as well as an ostomy coupling is provided. The locking ring includes two extension arms (4,5) connected at a common fulcrum (6) that will act as a hinge, when the arms are rotated with respect to each other. A toggle-mechanism may be used in the locking ring. The extension arms will through a connection to the locking ring close the locking ring upon rotation.

20 Claims, 3 Drawing Sheets

(56) References Cited

U.S. PATENT DOCUMENTS

| | | | | |
|---|---|---|---|---|
| 5,364,379 | A | | 11/1994 | Ozenne |
| 5,496,297 | A | * | 3/1996 | Olsen ...................... A61F 5/448 604/338 |
| 5,647,861 | A | * | 7/1997 | Steer ...................... A61F 5/448 215/279 |
| 5,902,295 | A | * | 5/1999 | Steer ...................... A61F 5/448 604/332 |
| 5,957,905 | A | * | 9/1999 | Steer ...................... A61F 5/448 604/338 |
| 2002/0165507 | A1 | * | 11/2002 | Hessel .................... A61F 5/448 604/342 |
| 2009/0118687 | A1 | * | 5/2009 | Kristensen ............. A61F 5/448 604/342 |
| 2014/0324003 | A1 | * | 10/2014 | Becker .................. A61F 5/448 604/342 |
| 2015/0045755 | A1 | * | 2/2015 | Pedersen ................ A61F 5/448 604/342 |

* cited by examiner

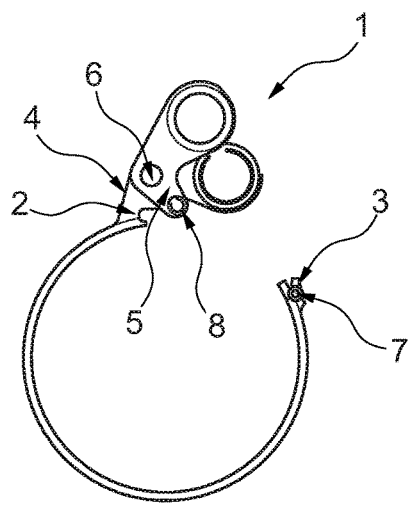
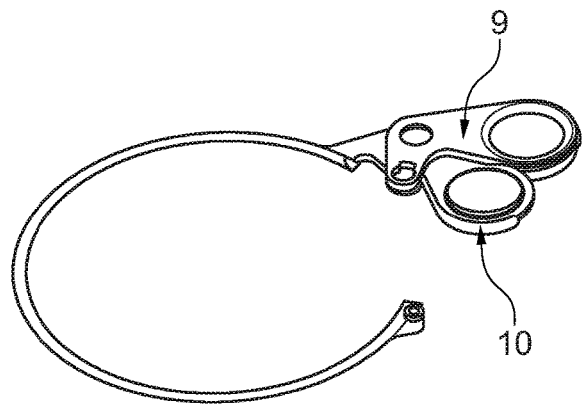
Fig. 1A            Fig. 1B
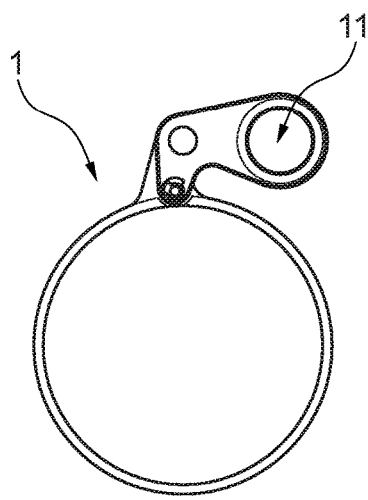
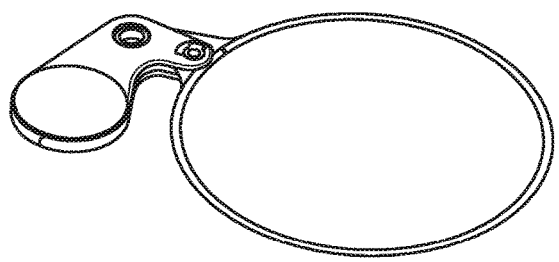
Fig. 2A            Fig. 2B

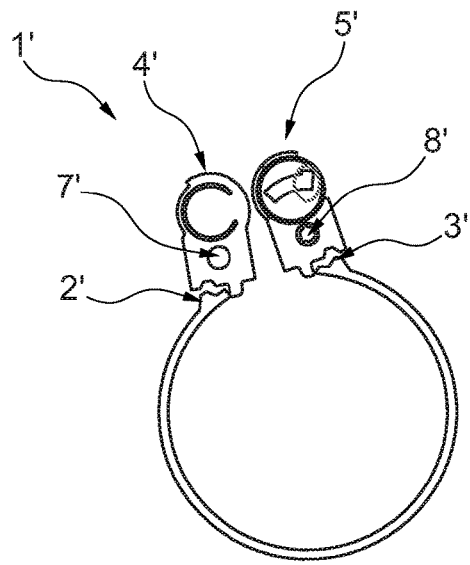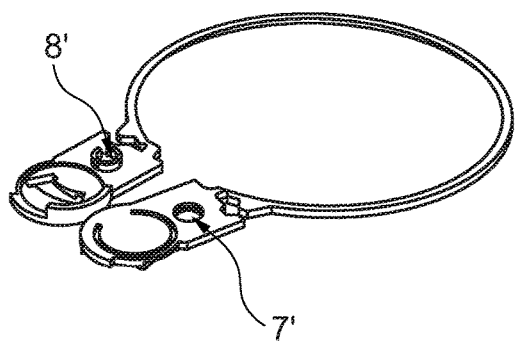
Fig. 3A    Fig. 3B
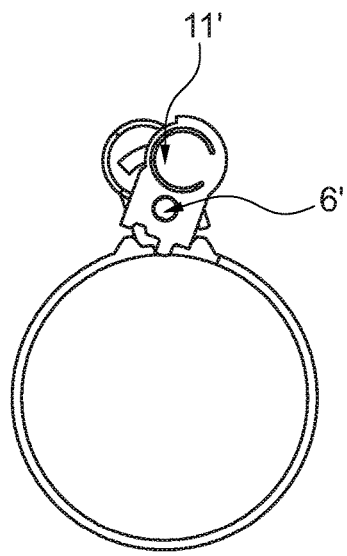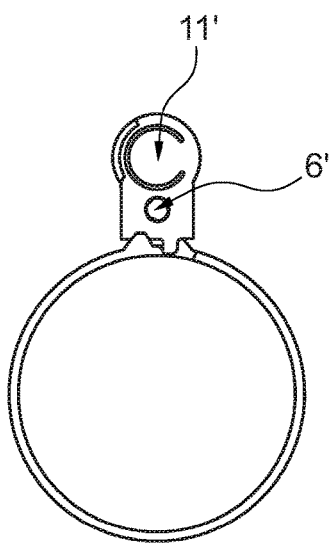
Fig. 4A    Fig. 4B

LOCKING RING WITH LEVER ARM

The invention relates to a locking ring for a coupling for an ostomy bag. The locking ring comprises a lever arm to make it easier to close the ring completely. The invention also relates to an ostomy appliance having a coupling with a locking ring provided with a lever arm.

BACKGROUND

In connection with surgery for a number of diseases in the gastro-intestinal tract, one of the consequences in many cases is that the patient is left with an abdominal stoma, such as a colostomy, an ileostomy or a urostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time.

An ostomy appliance may be in the form of a one-piece appliance for which a collecting bag for human body wastes is permanently, or fixedly, secured to an adhesive base plate for attachment to the human skin. Alternatively, the ostomy appliance may be a two-piece appliance comprising a base plate and a collecting bag which may be coupled to and uncoupled from each other through a coupling means. This has the effect that the base plate does not need to be separated from the skin of the user as often as exchange of the collecting bag requires. The base plate may need only to be changed every third or fourth day depending on the user, whereas the collecting bag may be changed more than once per day. Typically, it is desirable to need as few exchanges of the base plate as possible in order to reduce the risk of skin complications.

For two-piece appliances, the coupling means between the base plate and the collecting bag is typically either an adhesive coupling comprising an adhesive layer on the collecting bag or a mechanical coupling comprising cooperating coupling means on the base plate and the collecting bag. This invention relates to a mechanical coupling between the base plate and the collecting bag—and in particular to a locking ring for such a coupling.

DESCRIPTION OF RELATED ART

International patent application no. WO 94/18919 describes an ostomy coupling comprising two annular coupling parts and a locking ring, where the first coupling part comprises a collar having a radially outwardly projecting annular edge for forming a groove with an in radial direction innermost groove section, and an annular recess positioned in its in radial direction inner side, and the second coupling part comprises an axially projecting part having an annular radially outwardly projecting beak being capable of engaging with the annular recess in the first coupling part. The locking ring is positioned in the groove of the first coupling part, so that its innermost diameter when it is in its locked position is smaller than the largest beak diameter of the second coupling ring.

U.S. Pat. No. 5,364,379 discloses an ostomy appliance comprising a base plate and a collecting bag, wherein the bag is fixed on the base plate by deforming sealing means whose radial size is increased by operating an appropriate actuator device. The actuator device may comprise a toggle mechanism.

SUMMARY OF THE INVENTION

The invention relates to a locking ring for use in a coupling for an ostomy appliance, where the circumference of the locking ring can be made smaller by rotating extension arms provided at the locking ring around a common rotation point or fulcrum functioning as a hinge-element. In other words, the two extension arms are connected through a toggle-mechanism. The rotation of the extension arms assures that the locking ring will be completely closed and locked, when the arms are in the locked position. In particular, because the circumference or the radial extent of the locking ring is reduced, such a locking ring will provide a complete closure at the entire periphery of the locking ring. When the locking ring is used in connection with a coupling for an ostomy appliance, the locking ring is positioned in a radial extending groove on one coupling member. The groove is adapted to fit against an axially upstanding rim with a radial extending flange on the other coupling member. Thus reducing the circumference of the locking ring will provide a sealing effect between the groove and the rim on the coupling. This means that a locking ring according to the invention will be able to provide a tight sealing around the entire periphery of the coupling, thus reducing or even eliminating the leakage at the coupling. The invention also relates to a coupling for an ostomy appliance with a locking cam fitting in a notch and where a locking ring as described above will keep the cam and notch fitted together in the locked position.

DETAILED DESCRIPTION OF THE INVENTION

In a first aspect, the invention relates to a locking ring for a coupling for an ostomy appliance, the locking ring being adapted to assume a first open position with a first circumference and a second locked position with a second smaller circumference, the locking ring is provided with a first arm and a second arm extending radially out from the locking ring and being attached to each other at a common fulcrum so that upon rotation of the first arm with respect to the second arm, the locking ring shifts from the first open position to the second locked position.

The first and second circumferences are defined as the circumference of the locking ring with respect to a common centre axis. This common centre axis will, when the locking ring is positioned on a coupling for an ostomy appliance, be coinciding with the central axis of the coupling. The first open position may also be defined as the locking ring having a first radial extent that is larger than a second radial extent, when the locking ring is in the second locked position.

The first and second arms being attached to each other at a common fulcrum assist in closing the locking ring to shift it into the second locked position. This is because the rotation about the fulcrum provides a lever arm between the fulcrum and the closure points at the circumference of the locking ring. Thus a force applied at the end of the arms will provide a sealing force at the closure points so that it is ensured that the locking ring is completely closed around the entire periphery—and in particular that no slit will be present, even at the closure points. A slit in the locking ring may lead to leakage through the coupling at the slit. Thus a locking ring as claimed provides a safe and reliable locking effect around the entire periphery of the coupling and reduces or even eliminates leakage through the coupling.

Another way of defining the locking ring may be: A locking ring for a coupling for an ostomy appliance, the locking ring being adapted to assume a first open position with a first circumference and a second locked position with a second smaller circumference, the locking ring is provided with a first arm and a second arm extending radially out from the locking ring and being provided as a toggle-mechanism with a common fulcrum as the hinge, so that upon rotation of the first arm with respect to the second arm, the locking ring undergoes a transition from the first open position to the second locked position.

A toggle-mechanism provides the possibility of directing a small force applied at one point to create a larger force applied at another point. For the locking ring, this means that the user can apply a relatively small force to the extensions and thus create a larger sealing force at the joint between the closure points of the locking ring.

When the locking ring is in the second locked position, the two closure points from which the first and second arm extends out from the locking ring, will be in sealing contact or even overlay each other. In other words the locking ring may be generally C-shaped with respect to the central axis for the locking ring and terminate in two closure points and is further provided with first and second arm extending out from the two closure points.

Another aspect of the invention relates to a coupling for an ostomy bag that comprises a
 a first coupling member comprising
  a notch
  a radially outwardly extending receiving channel
  a locking ring as described above
 a second coupling member comprising
  a rib upstanding in the axial direction the rib being provided with a locking cam
 wherein the locking cam of the second coupling member cooperates with the notch on the first coupling member
 the locking ring being received in the radially outwardly extending channel.

Yet another aspect of the invention relates to an ostomy appliance comprising a collecting bag with a first coupling member as defined above and a base plate with a second coupling member as defined above. In an embodiment, the collecting bag may be provided with the second coupling member and the base plate with the first coupling member.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is substantially perpendicular to the abdominal surface of the user.

The radial direction is defined as transverse to the axial direction that is transversely to the direction of the stoma.

By attached is meant that two parts can be either permanently attached to each other—as by riveted together, glued together or welded together—or releasably attached to each other—as by snapped or fitted together. Other ways of providing both a permanently attachment and a releasably attachment is well-known in the art.

An ostomy appliance is well-known in the art. The collecting bag usually comprises a front wall on the distal side and a rear wall on the proximal side. The walls are made of gas- and liquid impermeable foil-material (for example of polyethylene (PE), polyvinyl-chloride (PVC) or ethylene-vinyl-acetate (EVA)) that is welded around the edges or the rim so as to form a pouch defining a waste collection chamber. The bag may be welded only partly around the rim so that an opening for emptying the bag is provided at the bottom of the bag. In that case the bag may be provided with means for closing that opening. The waste inlet opening is provided in the rear wall and placed in the upper part of the collecting bag so that when a user stands up, the waste inlet opening will be above the midline of the collecting bag. This leaves a larger collecting volume below the waste inlet opening. Thus, the top of the collecting bag is defined as the part closest to the waste inlet opening, and the bottom is defined as the opposite part.

The first coupling member includes a channel, which generally is U-shaped with the legs of the U extending radially out from the stoma when the appliance is fitted at the user.

The first coupling member may be on the bag or at the wafer and the second coupling member on the other.

The first coupling member may be made of a relatively flexible material, for example low-density Polyethylene (LDPE). As an example of a suitable material, a material such as Exact® 0230, which is an ethylene based octene plastomer, may be used. This material has a flexural modulus of approximately 67 MPa, when measured according to ISO 178, which is contemplated to be a satisfactory level.

The second coupling member may be made of rigid material such as Polypropylene (PP).

The second coupling member may also be made by two components, for example in two-shot injection moulding process. In this case a locking part may be made of a rigid material, for example PP and an attachment part may be made of a flexible material, for example LDPE. The locking part then includes the locking cam adapted for cooperating with a notch in the first coupling member and the attachment part has the flange for welding the second coupling member to the wafer of the ostomy appliance. In this way the coupling will be more flexible when it is in the assembled or coupled position. As an example the locking part may be made of a PP-material, Sabic® 58MNK 10, and the attachment part may be made of a LDPE material as the one described for use with the first coupling member. The PP material has a flexural modulus of approximately 1650 MPa, when measured according to ASTM D790, which is contemplated to be a satisfactory level for the locking part.

The cooperation between the notch on the first coupling member and the locking cam on the second coupling member may be as described in the international patent application no. WO9418919.

The locking ring may be made of PP. The two arms connected at the common fulcrum may also be known as a toggle-mechanism with a hinge as the common fulcrum. The hinge (or common fulcrum) may be made as any rotational connection well-known in the art. The only limitation to the connection is that the two arms should be able to rotate around the connection. The connection will not be described further.

In an embodiment of the invention, the lengths of the first and second arms are shorter from the locking ring to common fulcrum than the lengths that extend radially beyond the common fulcrum. In other words, the first and second arms have first parts extending from the locking ring to the fulcrum and second parts extending from the fulcrum and to the ends of the first and second arms, respectively. In this embodiment, the first parts of the first and second arms are shorter than the second parts of the first and second arms.

This embodiment provide for an easy to close locking ring because of the utilisation of lever arms to closure, so that a relatively low applied force to the ends of the first and second arms will result in larger force at the closure points.

In an embodiment of the invention, the second parts of the first and second arm extend at an angle to the first parts of the first and second arms, wherein the second parts are provided with locking means for locking the first and second arm in the locked position of the locking ring.

Angled arms may provide a coupling with a generally smaller radial extent, because the locking means can be provided closer to the periphery of the locking ring, when the arms are angled. This means that the coupling may generally be less conspicuous.

BRIEF DESCRIPTION OF THE DRAWING

FIGS. 1A, 1B illustrate an embodiment of a locking ring according to the invention in an open position. FIG. 1A is planar view seen from the front; FIG. 1B is a perspective view.

FIGS. 2A, 2B illustrate the same embodiment as in FIGS. 1A, 1B, but with the locking ring in a closed position. FIG. 2A is a planar view seen from the front; FIG. 2B is a perspective view.

FIGS. 3A, 3B illustrate another embodiment of a locking ring according to the invention in an open position. FIG. 3A is a planar view seen from the front; FIG. 3B is a perspective view FIGS. 4A, 4B illustrate the same embodiment as in FIGS. 3A, 3B with the locking ring in a semi-closed (FIG. 4A) and a fully closed position (FIG. 4B).

DETAILED DESCRIPTION OF THE DRAWING

Figure 5:
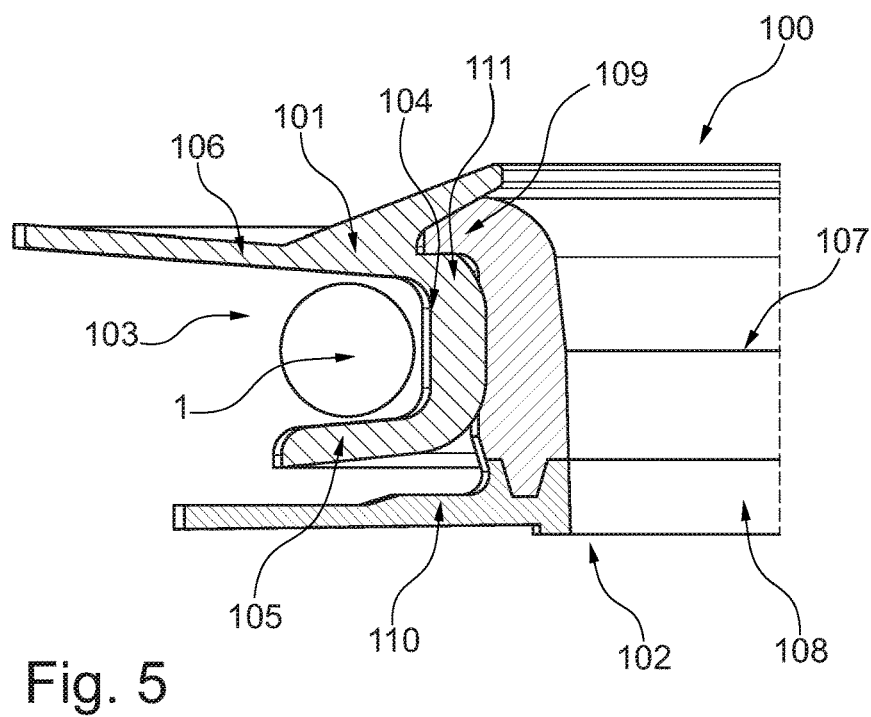
FIGS. 5 and 6 illustrate cross-sectional views of embodiments of a coupling with a locking ring inserted.

FIGS. 1A, 1B, 2A and 2B illustrate a locking ring 1 according to the invention. In a FIG. 1A, 1B the locking ring is shown in the open position and FIGS. 2A, 2B illustrate the locking ring in the closed or locked position.

The locking ring 1 is generally C-shaped with respect to a central axis and terminates in two closure points 2, 3. The locking ring 1 further comprises a first arm 4 connected to the first closure point 2 and a second arm 5 adapted for being connected to the second closure point 3. In the illustrated embodiment, the first and second arm 4, 5 are connected to each other at a common fulcrum 6 in form of a rotational connection. In other embodiments, the second arm 5 is connected to the second closure point 3 and adapted for being connected to the first arm 4 at the common fulcrum 6. Such a connection may be made by a simple snap-fitting. The common fulcrum 6 divides the first and second arm into first parts 7, 8 and second parts 9, 10. In the illustrated embodiment the first parts 7, 8 are shorter than the second parts 9, 10.

In the illustrated embodiment, the connection between the second arm 5 and the second closure point 3 is done by a ring 11 and a tap 12 fitting in the ring 12. However, many other types of connections are suitable as long as the connection allows movement in the planar direction of FIG. 1A to be transferred from the second arm 5 through the second closure point 3 to the locking ring 1.

In the embodiment of FIGS. 1A, 1B, 2A, 2B the second parts 9, 10 extend at an angle (in the illustrated embodiment approximately 90 degrees) with respect to first parts 7, 8 of the first and second arms. The second parts 9, 10 comprise a snap-fitting 13 to keep the locking ring in a locked position.

When a locking ring as shown in FIGS. 1A, 1B, 2A, 2B is to be used, the user hooks the tap 12 in the ring 8, turns the second part 10 with respect to the second part 9 and thereby the second arm 5 with respect to the first arm 4 until the snap-fitting 13 locks the arms with respect to each other and thus brings the locking ring 1 into the locked position.

FIGS. 3A, 3B, 4A, 4B illustrate another embodiment of a locking ring 1' according to the invention. This locking ring 1' is very similar to the locking ring 1 of FIGS. 1A, 1B, 2A and 2B. The locking ring 1' is provided with a first arm 4' and a second arm 5', connected to the locking ring 1' at a first and second closure point 2', 3'. In this embodiment the first and second arm 4', 5' are detachably connected to each other at the common fulcrum 6'. The connection is done by a ring 11' and a tap 12'. The first and second arm 4', 5', includes the snapfitting 13' to keep the locking ring in the locked position. Thus, the embodiment illustrated in FIGS. 3A, 3B, 4A and 4B does not include extension arms.

When a locking ring as shown in FIGS. 3A, 3B, 4A, 4B is to be used, the user hooks the two arms 4', 5' to each other by entering the tap 12' into the ring 11'. In this position the locking ring is in the position shown in FIG. 4A. Then the user rotates the first and second arm 4', 5' with respect to each other until the snap-fitting 13' locks the arms and brings the locking ring 1' into the locked position.

FIG. 5 illustrates a cross sectional view of a coupling 100 according to the invention. The coupling has a first coupling member 101 and a second coupling member 102. The first coupling member 101 may be welded to the ostomy bag and the second coupling member 102 may be welded to the base plate. The first coupling member 101 is provided with a receiving channel 103 extending radially outwards from the inner periphery 104 of the coupling. The first coupling member further has flanges; a flange 105 adapted for containing the locking ring in the coupled position of the coupling and a flange 106 adapted for being welded to the collecting bag (not shown). These two flanges form the legs of the receiving channel. The first coupling member further includes a notch 111 for receiving a locking cam 109 of the second coupling member.

The second coupling member 102 comprises in the shown embodiment a locking part 107 of a relatively rigid material and an attachment part 108 of a more flexible material. These two together defines an upstanding rib extending in the axial direction with respect to the stoma. The locking part 107 includes a locking cam 109 and providing this part of a more rigid material helps prevent unintentional uncoupling of the coupling parts. The flexible attachment part 108 includes a flange 110 adapted for being welded to the base plate of an ostomy appliance. By providing a part of the second coupling member of a more flexible material, the coupling will overall be more flexible and thus more comfortable for the user. However, the second coupling may be made entirely of a relatively rigid material.

In a first uncoupled position of the coupling, the locking ring 1 will be received relatively loosely in the receiving channel 103. In this position, the first coupling member 101 may be attached to and released from the second coupling member 102. When the coupling is to be coupled, initially, the first coupling member 101 with the locking ring 1 in the receiving channel 103 is attached to the second coupling member 102 so that the locking cam 109 is received in the notch 111. When it is ensured that the locking cam 109 is fitted correctly in the notch 111 around the entire periphery, the locking ring 1 is shifted from the first unlocked position to the second locked position. In the position shown in FIG. 5, the coupling parts 101, 102 are illustrated in the coupled position and the locking ring 1 (in the locked position) keeps the locking cam 109 and the notch 111 on the first coupling part connected to each other. In this position, the cooperation between the locking ring at the first coupling member and the locking cam at the second coupling member prevents the two parts from being uncoupled. Furthermore, the flexible material at the notch 111 provides a sealing effect between the two coupling parts so as to prevent output from the stoma from travelling through the coupling.

In FIG. 5, the locking ring 1 is illustrated as being circular in cross-section—however the cross-section may take many forms such as angular with any number of sides for example 3, 4 or 6 or oval or ellipsoid or any other rounded shape.

Figure 6:
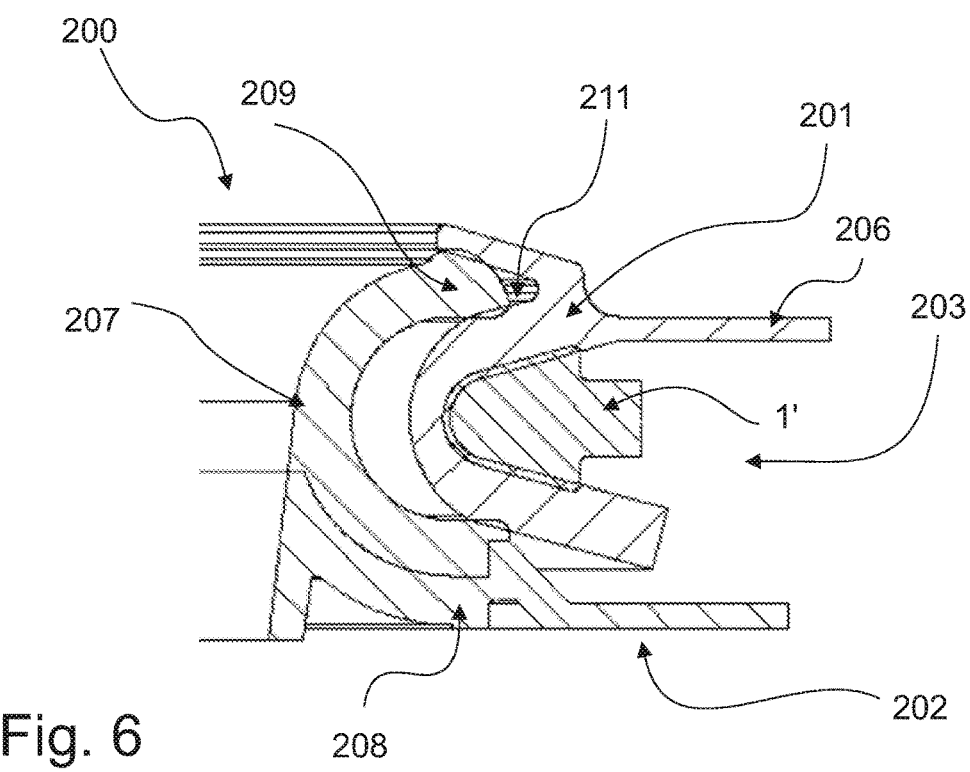

Another embodiment of a coupling 200 according to the invention is illustrated in FIG. 6. This coupling 200 also has a first coupling member 201 and a second coupling member 202. The first coupling member 201 is in this embodiment generally C-shaped in cross-section and has a receiving channel 203 inside the C-shape. The first coupling member is provided with a flange 206 for welding to the collecting bag. The second coupling member 202 is also generally C-shaped in cross section. Like illustrated in the embodiment of FIG. 5, this second coupling member 202 may also have an upstanding rib made of two parts 207, 208 having differing rigidity, so that the attachment part 208 welded to the base plate is more flexible than the locking part 207 providing the locking with the first coupling member 201. The locking part 207 comprises a locking cam 209 adapted to cooperate with a notch 211 on the first coupling member like it is described with respect to the embodiment in FIG. 5. The locking ring 1' is in this embodiment preferably shaped like an arrow-head in cross-section. Thereby, when the first and second coupling member 201 and 201 are attached to each other, and the locking ring 1' is locked, the locking ring 1' will push the C-shaped first coupling member 201 into sealing contact with the second C-shaped coupling member. This will provide sealing towards the top as well as towards the bottom in cross section in the figure (that is in axial directions with respect to the stoma)—thereby generally improving the sealing of the coupling.

The invention claimed is:

1. A locking ring for a coupling component of an ostomy appliance, the locking ring comprising:
  a ring element and a lock element, the ring element extending between a first end portion having a first closure point and a second end portion having a second closure point, the lock element having a first arm connected to the first end portion of the ring element and a second arm that is directly attachable to the first arm at a common fulcrum to allow the second arm to rotate relative to the first arm about the common fulcrum;
  wherein, with the second arm connected to the second end portion and with the second arm serving as lever operable to pivot about the common fulcrum, the lock element is operable to move the ring element from a first open position to a second locked position;
  wherein, in the first open position, the first end portion is separated from the second end portion with the first closure point separated from the second closure point;
  wherein, in the second locked position, the first closure point is in sealing contact with the second closure point;
  wherein a first longitudinal axis of the first arm is configured to move from a non-parallel and non-overlapping position to a parallel and overlapping position, relative to a second longitudinal axis of the second arm, when the lock element moves the ring element from the first open position to the second locked position.

2. The locking ring of claim 1, wherein the second end portion of the ring element includes a projection provided separately from the second closure point, and when the ring element is in the second locked position, the projection of the second end portion of the ring element is retained within a recess formed in the second arm of the lock element to pivotably connect the second arm to the second end portion.

3. The locking ring of claim 1, wherein the second arm of the lock element is fixedly connected to the second end portion of the ring element, and the first arm and the second arm are operable to detachably connect at the common fulcrum.

4. The locking ring of claim 1, wherein the first arm and the second arm each extend radially out from, respectively, the first end portion and the second end portion.

5. The locking ring of claim 1, wherein the first arm and the second arm each have first parts extending from the ring element to the common fulcrum and second parts extending from the common fulcrum to ends of the respective one of the first arm and the second arm, the first parts of the first arm and the second arm being shorter than the second parts of the first arm and the second arm.

6. The locking ring of claim 5,
  wherein the second parts of the first and second arm extend at an angle to the first parts of the first arm and the second arm, and
  wherein the second parts are provided with locking means for locking the first and second arm in the locked position of the locking ring.

7. The locking ring of claim 1, wherein the second arm is adapted for being rotatably connected to the second end portion.

8. The locking ring of claim 7,
  wherein the second end portion includes a tap, and
  wherein the second arm includes a ring configured to hook the tap to forma connection to the second end portion.

9. The locking ring of claim 1,
  wherein the first arm is rotatably connected to the first end portion, and
  wherein the second arm is rotatably connected to the second end portion.

10. The locking ring of claim 9, wherein the first arm is detachably connected to the second arm at the common fulcrum.

11. The locking ring of claim 1, further comprising a snap-fitting between the first arm and the second arm to keep the ring element in the second locked position.

12. The locking ring of claim 1, wherein the common fulcrum is a snap-fitting connection between the first arm and the second arm.

13. A coupling for an ostomy bag comprising:
  a first coupling member comprising:
    a notch;
    a radially outwardly extending receiving channel; and
    a locking ring for a coupling component of an ostomy appliance, the locking ring comprising:
      a ring element and a lock element, the ring element extending between a first end portion having a first closure point and a second end portion having a second closure point, the lock element having a first arm connected to the first end portion of the ring element and a second arm that is directly attachable to the first arm at a common fulcrum to allow the second arm to rotate relative to the first arm about the common fulcrum;

wherein, with the second arm connected to the second end portion and with the second arm serving as lever operable to pivot about the common fulcrum, the lock element is operable to move the ring element from a first open position to a second locked position;

wherein, in the first open position, the first end portion is separated from the second end portion with the first closure point separated from the second closure point;

wherein, in the second locked position, the first closure point is in sealing contact with the second closure point;

wherein a first longitudinal axis of the first arm is configured to move from a non-parallel and non-overlapping position to a parallel and overlapping position, relative to a second longitudinal axis of the second arm, when the lock element moves the ring element from the first open position to the second locked position; and a second coupling member comprising:
a rib upstanding in the axial direction the rib being provided with a locking cam;
wherein the locking cam of the second coupling member cooperates with the notch on the first coupling member, the locking ring being received in the radially outwardly extended channel.

14. The coupling of claim 13, wherein the second end portion of the ring element includes a projection provided separately from the second closure point, and when the ring element is in the second locked position, the projection of the second end portion of the ring element is retained within a recess formed in the second arm of the lock element to pivotably connect the second arm to the second end portion.

15. The coupling of claim 13, wherein the ring element has a generally arrow-shaped cross section.

16. The coupling of claim 13,
wherein the first arm is rotatably connected to the first end portion, and
wherein the second arm is rotatably connected to the second end portion.

17. An ostomy appliance comprising:
a first coupling member comprising:
a notch;
a radially outwardly extending receiving channel; and
a locking ring for a coupling components of the ostomy appliance, the locking ring comprising:
a ring element and a lock element, the ring element extending between a first end portion having a first closure point and a second end portion having a second closure point, the lock element having a first arm connected to the first end portion of the ring element and a second arm that is directly attachable to the first arm at a common fulcrum to allow the second arm to rotate relative to the first arm about the common fulcrum;
wherein, with the second arm connected to the second end portion and with the second arm serving as lever operable to pivot about the common fulcrum, the lock element is operable to move the ring element from a first open position to a second locked position;
wherein, in the first open position, the first end portion is separated from the second end portion with the first closure point separated from the second closure point;
wherein, in the second locked position, the first closure point is in sealing contact with the second closure point;
wherein a first longitudinal axis of the first arm is configured to move from a non-parallel and non-overlapping position to a parallel and overlapping position, relative to a second longitudinal axis of the second arm, when the lock element moves the ring element from the first open position to the second locked position;
a second coupling member comprising:
a rib upstanding in an axial direction the rib being provided with a locking cam;
wherein the locking cam of the second coupling member cooperates with the notch on a first coupling member, the locking ring being received in the radially outwardly extended channel;
a collecting bag with the first coupling member; and
a base plate with the second coupling member.

18. The ostomy appliance of claim 17, wherein the second end portion of the ring element includes a projection provided separately from the second closure point, and when the ring element is in the second locked position, the projection of the second end portion of the ring element is retained within a recess formed in the second arm of the lock element to pivotably connect the second arm to the second end portion.

19. The ostomy appliance of claim 17,
wherein the first arm is rotatably connected to the first end portion, and
wherein the second arm is rotatably connected to the second end portion.

20. The ostomy appliance of claim 17,
wherein the first coupling member is welded to the collecting bag, and
wherein the second coupling member is welded to the base plate.

* * * * *